United States Patent [19]

VandenBerg

[11] Patent Number: Plant 7,586

[45] Date of Patent: Jul. 9, 1991

[54] CHRYSANTHEMUM PLANT NAMED SARAH

[75] Inventor: Cornelis P. VandenBerg, Salinas, Calif.

[73] Assignee: Yoder Brothers, Inc., Barberton, Ohio

[21] Appl. No.: 459,365

[22] Filed: Dec. 29, 1989

[51] Int. Cl.[5] ..... A01H 5/00

[52] U.S. Cl. ..... Plt./78

[58] Field of Search ..... Plt./76, 78

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Sarah particularly characterized by its flat capitulum form; quilled decorative capitulum type; yellow-orange ray floret color; diameter across face of capitulum of from 63 to 75 mm when fully opened; average plant height with spreading and prolific branching pattern; average natural season flowering date of September 4 in Salinas, Calif. and October 5 in Hightstown, N.J.; uniform eight week photoperiodic flowering response to short days in photoperiodic controlled flowering programs; and durable, uniform performance.

3 Drawing Sheets

The present invention comprises a new and distinct cultivar of Chrysanthemum, botanically known as *Dendranthema grandiflora,* and referred to by the cultivar name Sarah.

Sarah, identified as 85-070004, was originated by the inventor Cornelis P. VandenBerg from a cross made in a controlled breeding program in Salinas, Calif., in 1985.

The female parent of Sarah was the cultivar identified as Debonair, a pink decorative disclosed in U.S. Plant Pat. No. 5,324. The male parent of Sarah was an unnamed seedling, identified as 80-N05003, and characterized by its heavily petalled single quill daisy form, and yellow flower color.

Sarah was discovered and selected as one flowering plant within the progeny of the stated cross by Cornelis P. VandenBerg in January 1986, in a controlled environment in Salinas, Calif.

The first act of asexual reproduction of Sarah was accomplished when vegetative cuttings were taken from the initial selection in April 1986 in a controlled environment in Salinas, Calif., by technicians working under the supervision of Cornelis P. VandenBerg.

Horticultural examination of controlled flowerings of successive plantings has shown that the unique combination of characteristics as herein disclosed for Sarah are firmly fixed and are retained through successive generations of asexual reproduction.

Sarah has not been observed under all possible environmental conditions. The phenotype may vary significantly with variations in environment such as temperature, light intensity and daylength.

The following observations, measurements and comparisons describe plants grown in controlled open areas in Salinas, Calif. and in Hightstown, N.J., and photoperiodic controlled programs conducted in Salinas, Calif. Rooted cuttings were established in soil and maintained outdoors under the natural temperature and daylength prevailing during June through October. Single pinching was practiced with all branches and buds retained.

The following traits have been repeatedly observed and are determined to be basic characteristics of Sarah, which, in combination, distinguish this Chrysanthemum as a new and distinct cultivar:

1. Flat capitulum form.
2. Quilled decorative capitulum type.
3. Butterscotch-bronze ray floret color.
4. Diameter across face of capitulum of 63–75 mm when fully opened.
5. Average plant height of 33 cm from soil line at time of flowering based on June 14 planting in Hightstown, N.J.
6. Spreading and prolific branching pattern, averaging 7–8 branches per plant after pinch two weeks after planting a rooted cutting in Hightstown, N.J.
7. Average natural season flowering date of September 4 in Salinas, Calif., and October 5 in Hightstown, N.J., based on several years of trial flowering.
8. Uniform eight week photoperiodic flowering response to short days in photoperiodic controlled flowering programs.
9. Durable, uniform performance.

The accompanying photographic drawings show typical inflorescence and leaf characteristics of Sarah, with the colors being as nearly true as possible with illustrations of this type.

Sheet 1 is a color photograph of Sarah grown as pinched spray pot mum in a 15 cm pot.

Sheet 2 is a black and white photograph of three views of the inflorescence of Sarah.

Sheet 3 is a black and white photograph showing the upper and under sides of the leaves of Sarah at three stages of development (mature, intermediate and immature).

The combination of capitulum type and ray floret color is not represented in any commercial garden mum cultivar known to the inventor. A cultivar with a capitulum type most similar in comparison to Sarah is the cultivar identified as Ballerina, a white quilled decorative disclosed in U.S. Plant Pat. No. 5,440. Reference is made to attached Chart A which compares certain characteristics of Sarah to the same characteristics of Ballerina.

Similar traits are capitulum form and a somewhat similar capitulum type. Sarah is yellow-orange, while Ballerina is white. Sarah also has a more spreading and prolific branching pattern, a slower controlled response, and a later natural season flowering date than Ballerina.

In the following description color references are made to the Royal Horticultural Society Colour Chart. The exact floret color of Sarah is not represented in the R.H.S. Colour Chart, and the color values given are those closest to the actual color of Sarah. The color values were determined on plant material grown in a controlled greenhouse environment in Salinas, Calif. on Sept. 20, 1989.

Classification:

*Botanical.*—*Dendranthema grandiflora* cv Sarah.

*Commercial.*—Quilled decorative spray pot mum and garden mum.

INFLORESCENCE

A. Capitulum:

*Form.*—Flat.

*Type.*—Quilled decorative.

*Diameter across face.*—63 to 75 mm when fully opened.

B. Corolla of ray florets:

*Color (general tonality from a distance of three meters).*—Yellow-orange.

*Color (upper surface).*—Open tubes near center 13A; open quills near periphery 13C.

*Color (under surface).*—Lower surface of outer quills closest to 13C.

*Shape.*—Tubular, straight.

C. Corolla of disc florets:

*Color (mature).*—14A to 14B.

*Color (immature).*—Yellow, tinged with 144C.

D. Reproductive organs:

*Androecium.*—Present on disc florets only; scant pollen.

*Gynoecium.*—Present on both ray and disc florets.

PLANT

A. General appearance:

*Height.*—Short.

*Branching pattern.*—Spreading and prolific.

B. Foliage:

*Color (upper surface).*—147A.

*Color (under surface).*—147B.

*Shape.*—See photograph.

CHART A

COMPARISON OF SARAH AND BALLERINA

| CHARACTERISTIC | SARAH | BALLERINA |
|---|---|---|
| Ray floret color | Yellow-orange | White |
| Capitulum Form and Type | Quilled decorative | Quilled decorative |
| Branching pattern | Spreading and prolific | Upright |
| Controlled Response | 8 weeks | 7 weeks |
| Average Natural Season Flower date: | | |
| In Salinas, California: | September 4 | August 27 |
| In Hightstown, New Jersey: | October 5 | September 29 |

Comparisons Made of Plants Grown Under Natural Season Outdoor Conditions In Salinas, California and in Hightstown, New Jersey

I claim:

1. A new and distinct Chrysanthemum plant named Sarah, as described and illustrated.

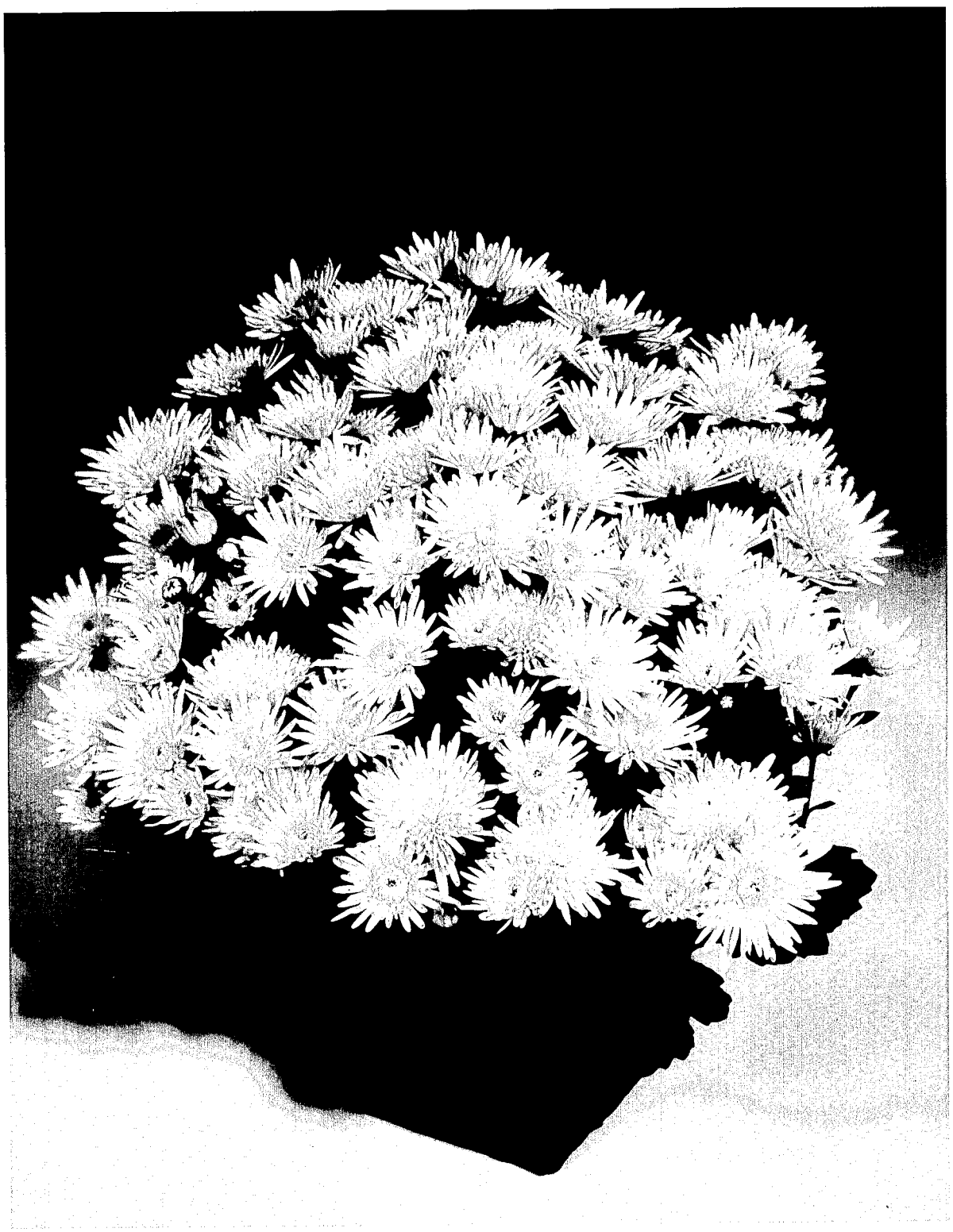

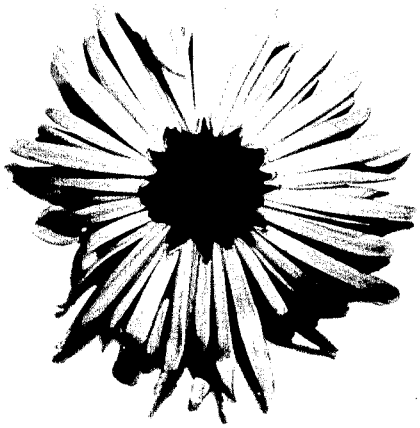
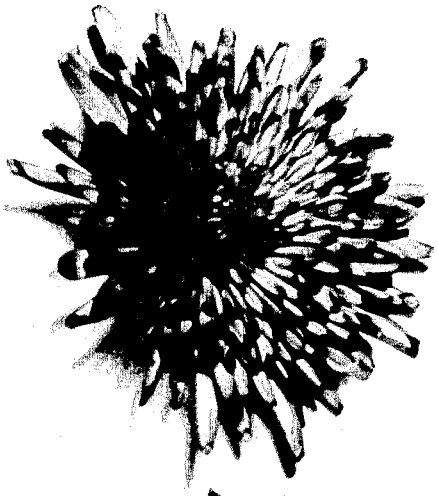
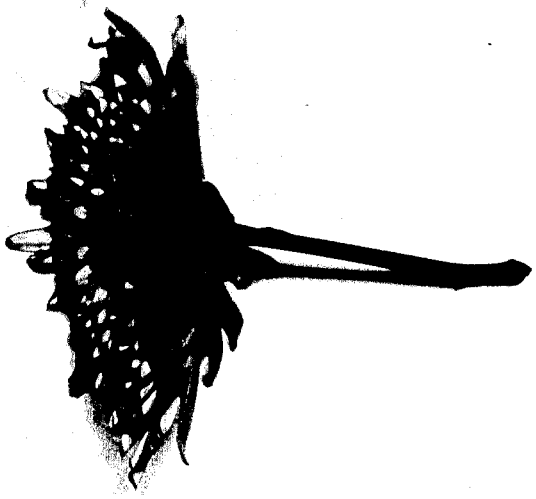

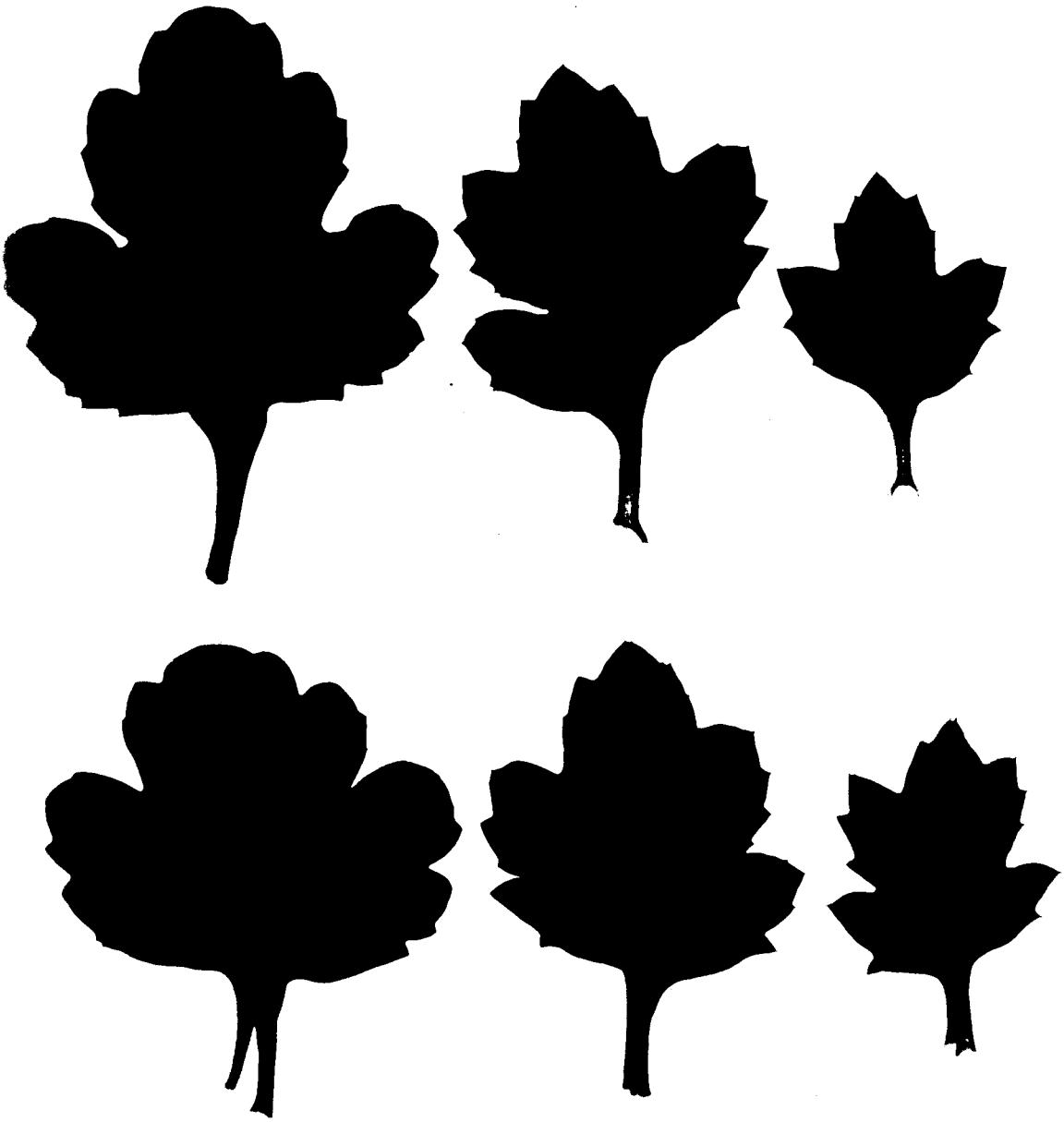

* * * * *